(12) United States Patent
Glomset et al.

(10) Patent No.: US 11,484,014 B2
(45) Date of Patent: *Nov. 1, 2022

(54) INTELLIGENT OXYGEN CONTROL IN SEA CAGES

(71) Applicant: Praxair Technology, Inc., Danbury, CT (US)

(72) Inventors: Kenneth Glomset, Alesund (NO); Stefan Dullstein, Neufahrn (DE); Thomas Loevold Hellebust, Valderoey (NO); John Bertil Aakernes, Aalesund (NO)

(73) Assignee: Praxair Technology, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/327,481

(22) PCT Filed: Aug. 24, 2017

(86) PCT No.: PCT/EP2017/025241
§ 371 (c)(1),
(2) Date: Feb. 22, 2019

(87) PCT Pub. No.: WO2018/041413
PCT Pub. Date: Mar. 8, 2018

(65) Prior Publication Data
US 2021/0345590 A1 Nov. 11, 2021

(30) Foreign Application Priority Data
Sep. 1, 2016 (EP) .................................... 16001910

(51) Int. Cl.
*A01K 63/04* (2006.01)
*C02F 1/00* (2006.01)
(Continued)

(52) U.S. Cl.
CPC ............ *A01K 63/042* (2013.01); *C02F 1/008* (2013.01); *C02F 1/727* (2013.01); *G01N 33/18* (2013.01);
(Continued)

(58) Field of Classification Search
CPC ...... A01K 63/042; A01K 63/04; G01N 33/18; G01N 33/1886; C02F 1/008; C02F 1/727;
(Continued)

(56) References Cited

U.S. PATENT DOCUMENTS 3,227,643 A * 1/1966 Okun .................... G01N 27/404
204/415
3,547,811 A 12/1970 McWhirter
(Continued)

FOREIGN PATENT DOCUMENTS

CN 204 697 754 U 10/2015
CN 105 320 187 A 2/2016
(Continued)

OTHER PUBLICATIONS

European Search Report for EP 16001910.5, dated Mar. 8, 2017, 8 pages.
(Continued)

*Primary Examiner* — Joseph W Drodge
(74) *Attorney, Agent, or Firm* — Donald T. Black

(57) ABSTRACT

The invention relates to a method for controlling a concentration of dissolved oxygen in a volume (V) of water (W), wherein a device (1) for dissolving oxygen in water (W) is submerged in said volume (V) of water, wherein oxygen is injected by the device (1) with an adjustable flow rate into a main water stream (W') sucked into a housing (100) of the device (1), and wherein the oxygen enriched main water stream (W') is discharged by the device (1) out of the housing (100) of the device (1) into said volume (V) of water (W), and wherein a current concentration of oxygen dissolved in the sucked main water stream (W') is measured with an oxygen probe (6) that is integrated into the housing (100) of the device (1), wherein said current concentration of dissolved oxygen is transmitted in a wireless fashion to a
(Continued)

Figure 1:
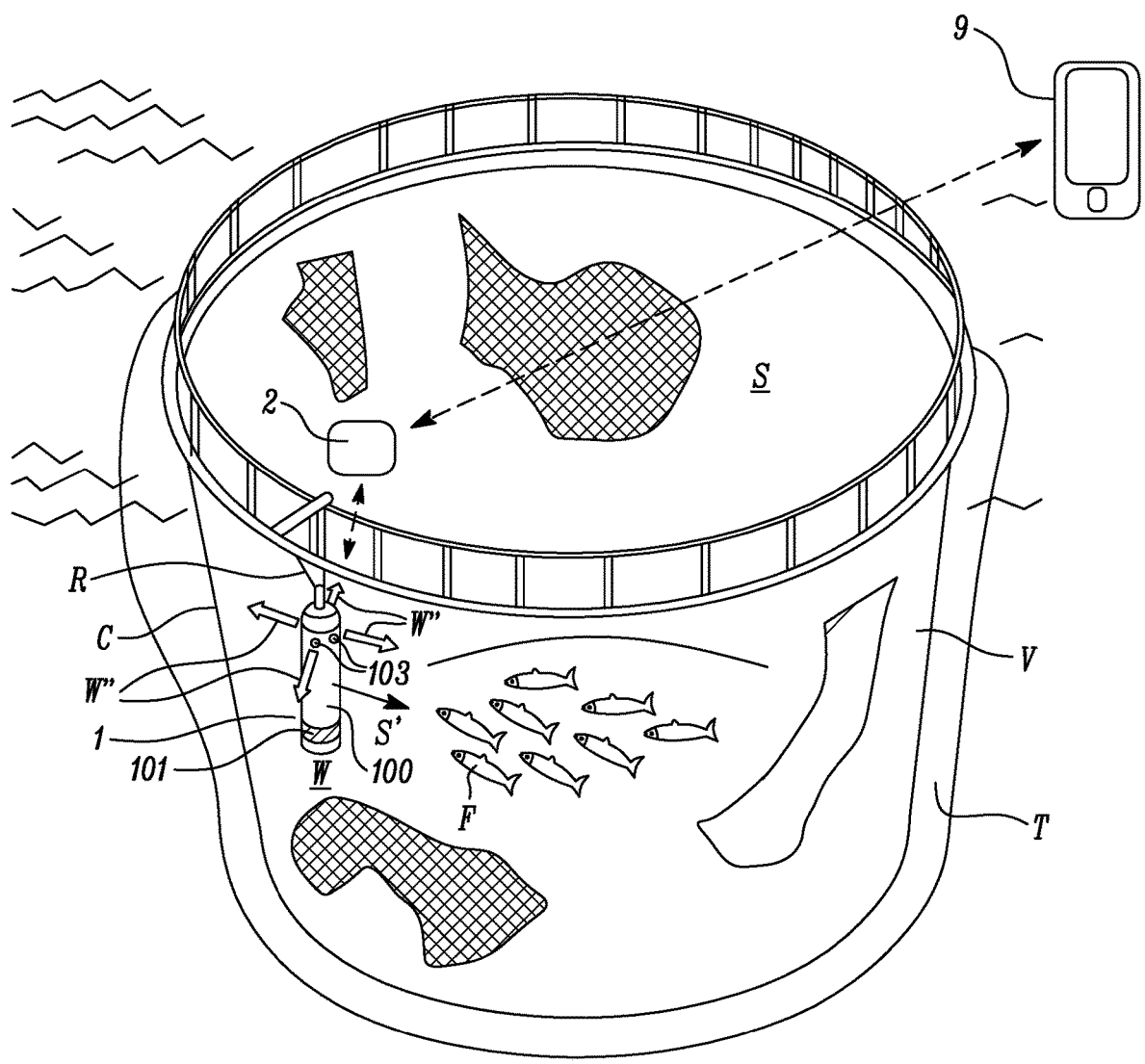

hand-held device (9) of an operator, and wherein the flow rate of the injected oxygen is controlled such that the measured current concentration of dissolved oxygen approaches a pre-defined reference value.

9 Claims, 3 Drawing Sheets

(51) Int. Cl.
*C02F 1/72* (2006.01)
*G01N 33/18* (2006.01)
*G05B 19/41* (2006.01)
*G05B 19/4155* (2006.01)
*C02F 103/20* (2006.01)
*G06Q 10/00* (2012.01)
*G06Q 50/02* (2012.01)

(52) U.S. Cl.
CPC ...... *G05B 19/4155* (2013.01); *C02F 2103/20* (2013.01); *C02F 2209/008* (2013.01); *C02F 2209/22* (2013.01); *C02F 2209/38* (2013.01); *G05B 2219/37371* (2013.01); *G06Q 10/30* (2013.01); *G06Q 50/02* (2013.01)

(58) Field of Classification Search
CPC .............. C02F 2209/38; C02F 2209/22; C02F 2209/008; C02F 2103/20; C02F 1/685; C02F 1/72; C02F 2209/225; G05B 19/4155; G05B 2219/37371; G05B 2219/37333; G06Q 10/30; G06Q 50/02; B01F 3/04099; B01F 3/04241; B01F 3/0446; B01F 5/0413; B01F 5/0425; B01F 5/0426; B01F 5/0428; B01F 5/043; B01F 15/0022
See application file for complete search history.

(56) References Cited

U.S. PATENT DOCUMENTS

| | | | |
|---|---|---|---|
| 3,713,274 A * | 1/1973 | Sauer | B01D 19/0042 96/157 |
| 3,839,902 A * | 10/1974 | Scott | B63B 22/18 73/61.51 |
| 3,983,031 A | 9/1976 | Kirk | |
| 4,246,111 A * | 1/1981 | Savard | C02F 3/006 210/96.1 |
| 5,329,719 A * | 7/1994 | Holyoak | A01K 61/60 43/6.5 |
| 5,582,777 A * | 12/1996 | Vento | A01K 63/042 261/121.2 |
| 6,120,008 A * | 9/2000 | Littman | A61L 2/18 261/76 |
| 6,443,097 B1 * | 9/2002 | Zohar | A01K 63/04 119/217 |
| 10,219,491 B2 * | 3/2019 | Stiles, Jr. | A01K 61/60 43/6.5 |
| 10,994,251 B2 * | 5/2021 | Glomset | B01D 47/10 |
| 2004/0154990 A1 * | 8/2004 | DeBusk | E02B 1/003 210/739 |
| 2007/0219652 A1 * | 9/2007 | McMillan | A01K 63/04 700/83 |
| 2010/0154717 A1 * | 6/2010 | Glomset | A01K 63/047 119/263 |
| 2011/0309034 A1 | 12/2011 | Yousfan et al. | |
| 2012/0024784 A1 * | 2/2012 | Clark | B01F 23/2322 210/151 |
| 2013/0082006 A1 * | 4/2013 | Clidence | B01F 23/2322 210/150 |
| 2013/0180460 A1 * | 7/2013 | Stiles, Jr. | A01K 61/00 119/227 |
| 2014/0311416 A1 * | 10/2014 | Stiles, Jr. | A01K 63/047 119/263 |
| 2014/0332464 A1 * | 11/2014 | Fabiyi | C02F 3/006 210/96.1 |
| 2015/0048032 A1 * | 2/2015 | Rodriguez | C02F 1/688 210/739 |
| 2016/0289088 A1 * | 10/2016 | Mo | B01D 47/10 |

FOREIGN PATENT DOCUMENTS

WO WO 2011/150463 A1 12/2011
WO WO 2018/041412 A1 3/2018

OTHER PUBLICATIONS

International Search Report for PCT/EP2017/025241, dated Nov. 22, 2017, Authorized Officer: Ismail Utku Kiyak, 2 pgs.
International Search Report for PCT/EP2017/025240, dated Nov. 8, 2017, Authorized Officer: Lucia Batres Arnal, 2 pgs.

* cited by examiner

INTELLIGENT OXYGEN CONTROL IN SEA CAGES

The invention relates to a method for controlling a concentration of dissolved oxygen in a volume of water, particularly in a sea cage for growing fish.

When growing fish it is usually mandatory to control the amount of oxygen in the water. Particularly when fish (e.g. salmon) is treated against sea lice in an open sea cage, it is favourable to add the oxygen consumption of the fish directly to the water. Usually this is done by dosing the oxygen gas through diffuser hoses that must be laid on the bottom of a tarp that closes the sea cage downwards and along its periphery.

The dosing is based on random or specific oxygen measurements done by workers on the site using hand-held oxygen probes.

Based on the above, the problem underlying the present invention is to provide an improved method for controlling a concentration of dissolved oxygen in water, particularly in a cage, container or pond used for growing fish.

This problem is solved by a method having the features of claim 1.

Preferred embodiments of the method are stated in the corresponding sub-claims and are described below.

According to claim 1 a method for controlling a concentration of dissolved oxygen in a volume of water is disclosed, wherein a device for dissolving oxygen in water is submerged in said volume of water, wherein oxygen is injected by the device with an adjustable flow rate into a main water stream sucked by the device into a housing of the device, and wherein the oxygen enriched main water stream is eventually discharged by the device out of the housing of the device into said volume of water, and wherein a current concentration of oxygen dissolved in the sucked main water stream is measured with an oxygen probe that is integrated into the housing of the device, wherein said current concentration of dissolved oxygen is transmitted in a wireless fashion to a hand-held device of an operator, and wherein the flow rate of the injected oxygen is controlled such, particularly by means of a control unit (e.g. PLC) that the measured current concentration of dissolved oxygen approaches a pre-defined reference value.

Thus, the invention allows to monitor the oxygen dosage at all times, in contrast to the usual procedure where the oxygen concentration is measured with hand-held oxygen probes. Due to the invention, particularly during sea lice treatment, while the chemical products are dosed into the cage, the staff can stay inside the cabin of the operation boat for safety reasons and still monitor the oxygen dosage which is not possible using manual oxygen measurements.

Furthermore, due to controlling injection of oxygen, less oxygen is needed since the dosage can be adapted to the precise demand. Furthermore, the invention allows in principle to automatically document the measured concentrations, e.g. as a documentation for fish welfare.

Further, according to a preferred embodiment of the method according to the invention, the pre-defined reference value is adjusted by an operator via said hand-held device which particularly communicates with said control unit. Particularly, the control unit is arranged close to the device, but above the water surface and connected to the probe and to a suitable actuator for adjusting the flow rate of the gas (e.g. by adjusting a valve), so that the flow rate can be controlled/adjusted by means of the control unit.

Further, according to a preferred embodiment of the method according to the invention, a temporal course of the reference value is set by an operator via said hand-held device. This means that the reference value can vary in a pre-defined manner during the time span over which oxygen is injected into the water.

Further, according to a preferred embodiment of the method according to the invention, the current concentration of dissolved oxygen and/or the current reference value and/or the temporal course of the reference value is displayed on a display of the hand-held device.

Further, according to a preferred embodiment of the method according to the invention, the measured current concentrations of dissolved oxygen are logged on the hand-held device for documentation.

Preferably, said hand-held device is a mobile phone, particularly a smart phone having a touchscreen.

Further, according to a preferred embodiment of the method according to the invention, said volume of water is enclosed by a tarpaulin arranged below and along the periphery of a cage submerged in the water. However, the method may also be applied to any other volume of water (e.g. a container or pond etc.)

Alternatively, the method according to the invention can also be applied to waste water treatment. Thus, according to an embodiment, the volume of water is a volume of waste water that is to be oxygenated using the method according to the invention.

According to yet another embodiment of the method according to the invention said device comprises:
- a housing, that is configured to be submerged into the water, wherein the housing comprises at least one water inlet, a gas inlet and at least one water outlet for discharging gas enriched water out of the housing,
- a pump that is in fluid communication with the at least one water inlet for sucking water from a surrounding of the housing, wherein the pump is configured to generate a main water stream,
- a means for injecting said gas supplied via said gas inlet into said main water stream, and
- said oxygen probe that is integrated into the housing of the device.

Particularly, the flow rate of the oxygen may be adjusted by means of a suitable valve which can be positioned either in the device or at a remote oxygen source from which oxygen is passed to the device via a suitable conduit. The valve may be actuated by said actuator that is connected to the control unit so that the flow rate can be controlled/adjusted by means of the control unit.

Furthermore, according to an embodiment of the method according to the present invention, the integrated oxygen probe comprises a measuring surface (e.g. a membrane or an optical surface), particularly at a tip of said probe, for measuring said current concentration.

Further, according to an embodiment of the method according to the present invention, the device directs a side water stream of the main water stream along said measuring surface for measuring said current concentration.

Thus, the invention allows to measure the oxygen concentration in the raw water getting into the device. Moreover, particularly, the invention ensures that the measuring point and the oxygenating point always have the same relation/distance to each other and can further be maneuvered to any position in the production volume.

Further, due to the fact that the probe is now integrated into the device, one can prevent that the probe gets hooked up to surrounding material, particularly fish nets and the like. Moreover, due to the integration of the oxygen probe into the housing of the device, the probe is completely protected against physical damage.

Further, according to an embodiment of the method according to the present invention, the device is configured to divert said side water stream from the main water stream downstream of the pump and upstream of the means for injecting said gas into the main water stream.

Further, according to a preferred embodiment of the present invention, for generating said side water stream, the device comprises a first orifice at a junction between a pump outlet pipe and said means for injecting oxygen into the main water stream, particularly at a location where said main water stream hits an inner surface of the device, such that said side water stream is forced through the first orifice, is flushed over the measuring surface of the probe, and is lead through a second orifice exiting the housing.

Further, according to a preferred embodiment of the method according to the present invention, the probe is configured to be arranged in a recess of the housing in a removable fashion, particularly such that when the probe is arranged in said recess, the measuring surface is arranged downstream the first orifice and upstream the second orifice so that said side water stream can be flushed over said measuring surface.

Further, according to a preferred embodiment of the present invention, the device comprises a closure means (e.g. a plastic part) that is configured to be arranged in a form fitting manner in said recess when the probe has been removed from the recess, wherein the closure means closes, particularly seals, the first orifice when it is arranged in the recess as intended, so that particularly no side water stream is generated.

Particularly, in an embodiment, said means for injecting the gas can be a Venturi nozzle that is in fluid communication with the pump on one end and with the at least one water outlet on the other end, wherein the nozzle comprises a constriction, wherein in the region of the constriction a fluid connection to said gas inlet is provide via which gas is sucked into the Venturi nozzle. Thus the nozzle ejects a gas enriched main water stream that is then discharged through the at least one water outlet, or divided into a number of partial streams that are discharged via a corresponding number of water outlets. Particularly, said inner surface that forces the side water stream through the first orifice can be an inner surface of said Venturi nozzle which protrudes inwards and towards a constriction of the Venturi nozzle so that the main water stream hits this inner surface and the side water stream is forced through the first orifice.

Particularly, the water outlets of the device are arranged on the housing such that upon discharging water (e.g. the main water stream) through said water outlets out of the housing, the repulsive forces cancel each other so that the housing can maintain essentially a constant position when submerged in water (apart from movements due to water drift).

Furthermore, the device particularly comprises a means for suspending the device at the top of the housing, particularly in the form of an eye.

Summarizing, the invention reduces the oxygen costs during dosage times due to a more responsive/exact dosing. Furthermore, due to the automated control of the oxygen dosing labour costs are reduced and separate handheld oxygen measuring equipment can be avoided.

Due to the automated control, the staff does not need to be close to the site at all times which increases operation safety, particularly during sea lice treatment.

Furthermore, shorter response times can be realized when the oxygen concentration drops or increases.

Finally, a reliable documentation of oxygen saturation during the whole time of oxygenation can be achieved.

Apart from submerged oxygen injection devices, the invention can also be used for fixed installations. In this case, the logged oxygen concentrations could be transferred to the operators hand-held device (e.g. mobile/smart phone) each time he passes near by the installation.

Figure 2:
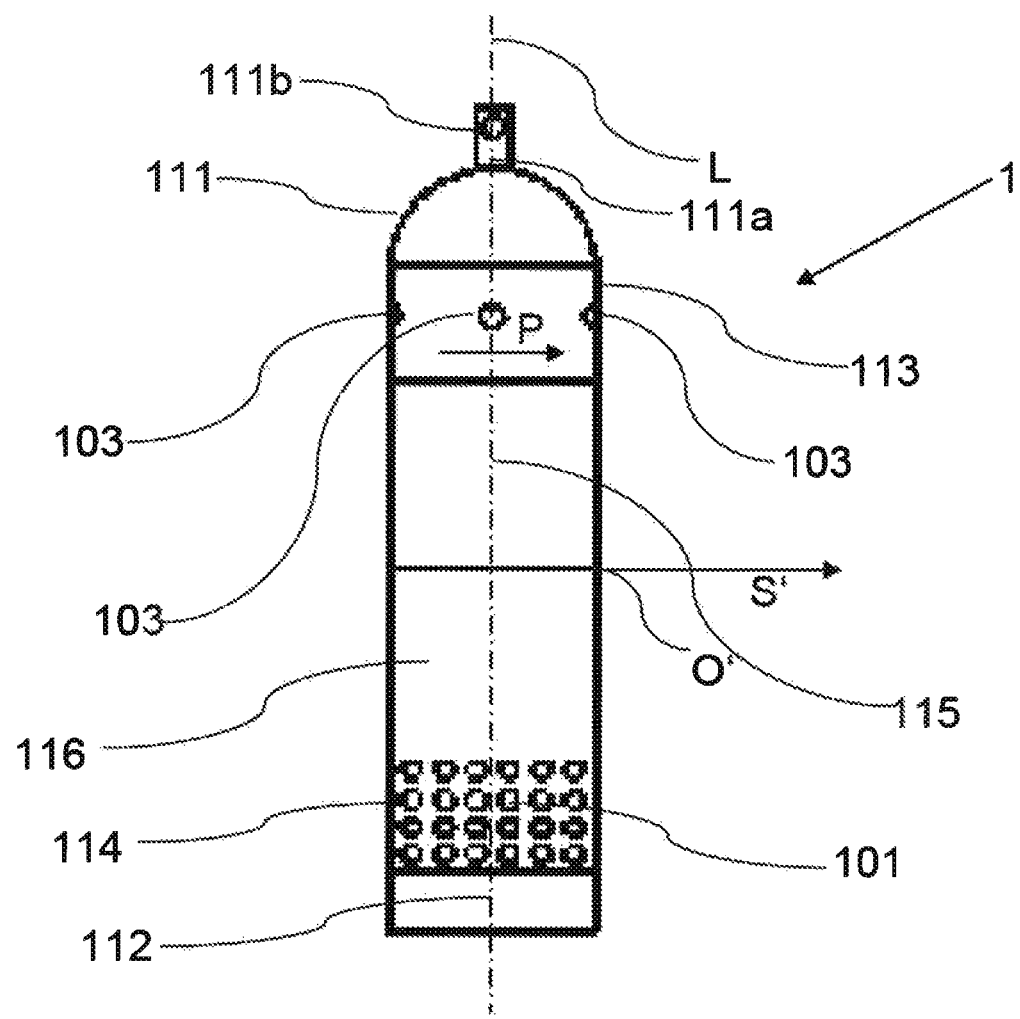
Figure 3:
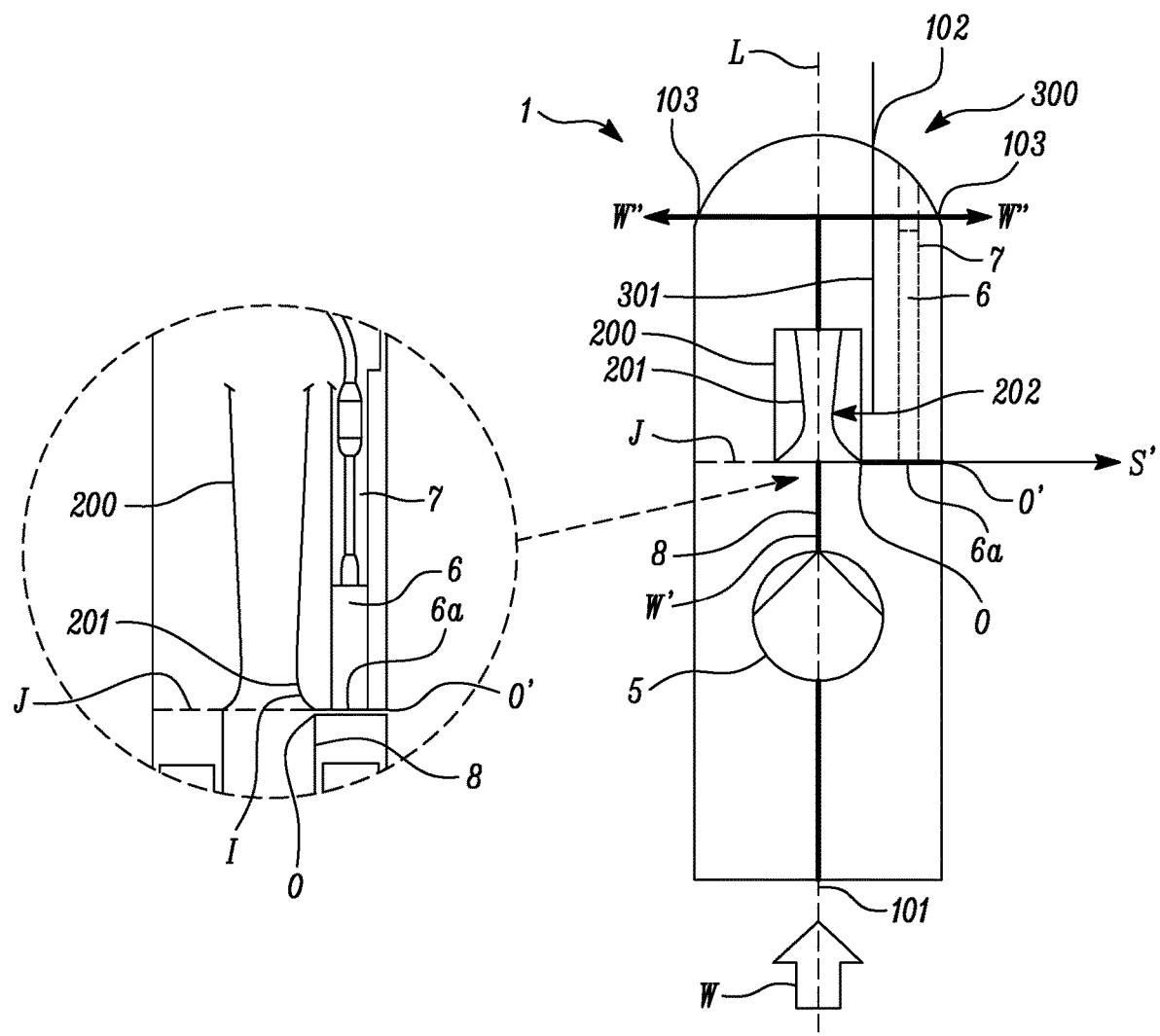

Further features, advantages and embodiments of the present invention shall be described in the following with reference to the Figures, wherein:

FIG. 1 an illustration of the method according to the invention, wherein oxygen in a submerged open sea cage is controlled using a control unit (e.g. PLC) and a hand-held device (e.g. a mobile phone, particularly smart phone);

FIG. 2 a schematical view of a device for dissolving oxygen in water that can be used in the method according to the invention; and FIG. 3 a schematical cross sectional view of the device shown in FIG. 2.

FIG. 1 shows a sea cage C submerged in a sea S that is closed by means of a tarpaulin T in order to define a finite volume V of water W into which oxygen shall be injected in a controlled manner. This can for instance be conducted during a treatment of the fish (e.g. salmon) against sea lice or at any other times in order to ensure an exact dosing of oxygen into the water W.

In order to control (e.g. by means of a feedback loop) a concentration of dissolved oxygen in said volume V, a device 1 for dissolving oxygen in water W is submerged in said volume V of water, wherein oxygen is injected by the device 1 with an adjustable flow rate into a main water stream W' sucked into a housing 100 of the device 1, and wherein the oxygen enriched main water stream W' is discharged by the device 1 out of the housing 100 of the device 1 into said volume V of water W, and wherein a current concentration of oxygen dissolved in the sucked main water stream W' is measured with an oxygen probe 6 that is integrated into the housing 100 of the device 1, wherein said current concentration of dissolved oxygen is transmitted in a wireless fashion from a control unit 2 (e.g. a programmable logic controller or PLC) that is connected to the probe 6 and to an actuator (not shown) for adjusting said flow rate, to a hand-held device 9 of an operator, wherein the flow rate of the injected oxygen is controlled such by the control unit 2 that the measured current concentration of dissolved oxygen approaches a pre-defined reference value. Particularly, the control unit 2 is arranged close to the device 1 above the water surface.

Preferably, the pre-defined reference value can be adjusted by said operator via said hand-held device 9 which is configured to communicate with the control unit 2. Particularly, said hand-held device 9 is a mobile phone, particularly smart phone.

Further, by means of said hand-held device 9, a temporal course of the reference value may be set by an operator. Furthermore, the hand-held 9 device may be used to display the monitored quantities like the current dissolved oxygen concentration in the water as well as to document (i.e. record) such quantities.

Particularly, as shown in FIGS. 2 and 3, the device 1 for dosing the oxygen into the water W comprises a housing 100, that is configured to be submerged into the water W in the cage C, wherein the housing comprises at least one water inlet 101, a gas inlet 102 that is connected to a suitable oxygen source so that a flow rate of the oxygen passing gas inlet 102 can be adjusted (e.g. by means of a valve at the gas inlet or at said oxygen source or at some other place, wherein the valve may be actuated by said actuator that is connected to the control unit 2), and at least one water outlet 103 for discharging gas enriched water W" out of the housing 100. Furthermore, the device 1 comprises a pump 5 that is in fluid communication with the at least one water inlet 101 for sucking water W from a surrounding of the housing 100, when the latter is submerged in the water W to be oxygenated, and wherein the pump 5 is configured to generate a main water stream W' that is passed via a pump outlet pipe 8 to a means 200 for injecting said gas G supplied via said gas inlet 102 into said main water stream W'. Particularly, said means 200 can comprise a Venturi nozzle for injecting the oxygen into the main water stream W'.

As already indicated above, the device 1 comprises an integrated oxygen probe 6 that is configured to measure a concentration of said gas, here oxygen, dissolved in water, wherein said probe 6 is arranged in the housing 100 of the device 1.

Particularly, the probe 6 comprises a measuring surface 6a, such as a membrane or an optical surface, for measuring the oxygen concentration in a known manner. Particularly, said surface 6a is arranged at a tip of the probe 6.

Preferably, the device 1 is configured to direct a side water stream S' of the main water stream W' along said measuring surface 6a. For this, the device 1 may comprise a first orifice O at a junction J between a pump outlet pipe 8 and said means (e.g. Venturi nozzle) 200, namely particularly at an inner surface I of said Venturi nozzle 200 that protrudes inwards towards a constriction 201 of said Venturi nozzle 200, such that said side water stream S' is forced through the first orifice O, is flushed over the measuring surface 6a of the probe 6, and is led through a second orifice O' out of the housing 100. Particularly, said main body 115 is also denoted as nozzle section 115 (see below) of the device 1 and comprises said means 200 for injecting said gas G.

Particularly, the probe 6 is configured to be arranged in a recess 7 of the housing 100 in a removable fashion, which recess 7 ends in the conduit that extends from the first orifice O to the second orifice O'. Thus, when the probe 6 is arranged in said recess 7, the measuring surface 6a is essentially flush with an inner side of the conduit and arranged downstream of the first orifice O and upstream of the second orifice O' so that said side water stream S' can be flushed in the conduit over said measuring surface 6a. Preferably, the device 1 further comprises a closure means e.g. in the form of a plastic part, that is configured to be arranged in a form fitting manner in said recess 7 when the probe 6 is not in use (and has been removed from the recess 7), wherein the closure means now blocks/seals the first orifice O when it is arranged in the recess 7, so that no side water stream S' is generated.

Particularly, the water outlets 103 of the device 1 are arranged on the housing 100 such that upon discharging water (e.g. the gas enriched water stream) W" through said water outlets 103 out of the housing 100, the repulsive forces cancel each other so that the housing 100 can maintain essentially a constant position when submerged in water.

The device 1 may comprise four such water outlets 103 which may be arranged along a periphery P of a shell 110 of the housing such that the outlets 103 are equidistantly spaced. Here, the outlets 103 may lie in a common plane that extends perpendicular to a longitudinal axis L of the housing 100/shell 110.

Preferably, the housing 100 is suspended from a rope R, wherein the rope may be connected to an eye 111b arranged at an upper end 111a of a cap 111 of the housing 100.

In detail, the housing 100 comprises a circumferential (e.g. cylindrical) shell 110 that extends along a longitudinal/cylinder axis L, wherein at the upper end of the housing the shell 110 connects to said cap 111, and wherein at a lower end of the housing 100 the shell 110 connects to a bottom 112. In case the device is suspended as described above, the longitudinal axis L extends vertically, as shown e.g. in FIG. 2.

The cap 111 may comprise an opening for receiving a cable that may comprise the gas supply 300. Further the cable may also comprise a power supply for the individual components of the device 1 as well as a data line. The gas supply 301 connects to the gas inlet 102 located on the cap 111 and extends from there to said means 200, e.g. to an inlet 202 of a constriction 201 of a Venturi nozzle 200 via which the gas G can be injected into the main water stream W'.

Along the longitudinal axis L the components of the (suspended) device 1 may be arranged as follows: The water inlets 101 are arranged above the bottom 112 on a lower section 114 of the shell Mantels 110 of the housing 100. The pump 5 is preferably arranged above the water inlets 101 in a pump section 116 of the housing shell 110/housing 100, wherein said means 200 (e.g. Venturi nozzle) is arranged above the pump in a nozzle section 115 (main body) of the housing 100/shell 110, namely below the water outlets 103 that are arranged on the upper section 113 of the shell 110.

The Venturi nozzle 200 may extend along the longitudinal axis L so that the main water stream W' can enter the nozzle from below, pass the constriction 201, where gas G is dosed into the stream W', and exits the nozzle 200 so that the gas enriched water W can be discharged via said water outlets 103, particularly so that the individual repulsive forces cancel each other (see above).

| Reference Numerals | |
|---|---|
| 1 | Device |
| 2 | Control unit (e.g. PLC) |
| 5 | Pump |
| 6 | Probe |
| 6a | Measuring surface |
| 7 | Recess |
| 8 | Pump outlet pipe |
| 9 | Hand-held device (e.g. mobile phone) |
| 100 | Housing |
| 101 | Water inlet |
| 102 | Gas inlet |
| 103 | Water outlet |
| 110 | Shell |
| 111 | Cap |
| 111a | Upper end |
| 111b | Eye |
| 112 | Bottom |
| 113 | Upper section |
| 114 | Lower section |
| 115 | Nozzle section (main body) |
| 116 | Pump section |
| 200 | Venturi nozzle |
| 201 | Constriction |
| 202 | Inlet |
| 300 | Gas supply |
| G | Gas |
| W | Water |
| W' | Main water stream/Gas enriched water |
| S | Sea |
| S' | Side water stream |
| C | Cage |
| F | Fish |
| P | Periphery |

-continued

| | Reference Numerals |
|---|---|
| O | First orifice |
| O' | Second orifice |
| J | Junction |
| I | Inner surface |
| T | Tarpaulin |

The invention claimed is:

1. A method for controlling a concentration of dissolved oxygen in a volume (V) of water (W), comprising:
submerging a device (1) for dissolving oxygen into the volume (V) of water;
sucking an incoming water stream (W) into a housing (100) of the device through a pump (5) for generating a main water stream (W');
injecting oxygen by the device (1) at an adjustable flow rate into the main water stream (W') in the housing (100);
discharging an oxygen enriched main water stream (W") from the device (1) out of the housing (100) into the volume (V) of water (W);
measuring a current concentration of oxygen dissolved in the main water stream (W') with an oxygen probe (6) integrated into the housing (100);
transmitting the current concentration of dissolved oxygen wirelessly to a hand-held device (9) of an operator; and
controlling the flow rate of the injected oxygen, such that the measured current concentration approaches a pre-defined reference value;
wherein the oxygen probe (6) comprises a measuring surface (6a) for measuring the current concentration of the dissolved oxygen;
wherein the measuring surface (6a) is at a tip of the oxygen probe (6); and
wherein the device (1) is configured to direct a side water stream (S') of the main water stream (W') from a first orifice O at a junction between an outlet pipe of said pump (5) and a means (200) for the injecting of the oxygen into the main water stream (W'), along the measuring surface (6a) for measuring the current concentration of the dissolved oxygen, and through a second orifice O' out of the housing.

2. The method of claim 1, further comprising adjusting the pre-defined reference value with the hand-held device (9).

3. The method of claim 1, further comprising setting a temporal course of the pre-defined reference value with the hand-held device (9) such that the reference value can vary in a pre-defined manner during a time span over which the oxygen is injected into the volume (V) of water (W) by the device.

4. The method of claim 3, further comprising displaying at least one of the current concentration of the dissolved oxygen, the pre-defined reference value, and the temporal course of the pre-defined reference value on a display of the hand-held device (9).

5. The method of claim 1, further comprising logging the measured current concentrations of the dissolved oxygen a plurality of times in the hand-held device (9) for documentation.

6. The method of claim 1, further comprising enclosing the volume (V) of the water (W) with a tarpaulin arranged below and along a periphery of a cage submerged in the water (W).

7. The method of claim 1, further comprising partly sealing the volume (V) of the water (W) with a skirt surrounding a cage submerged in the water (W).

8. The method of claim 1, wherein the volume (V) of water (W) comprises waste water.

9. In a method for controlling a concentration of dissolved oxygen in a volume (V) of water (W),
wherein the method includes;
submerging a device (1) for dissolving oxygen into the volume (V) of water,
sucking an incoming water stream (W) into a housing (100) of the device through a pump (5) for generating a main water stream (W'),
injecting oxygen by the device (1) at an adjustable flow rate into the main water stream (W') in the housing (100),
discharging an oxygen enriched main water stream (W") by from the device (1) out of the housing (100) into the volume (V) of water (W),
measuring a current concentration of oxygen dissolved in the main water stream (W') sucked into the housing with an oxygen probe (6) integrated into the housing (100),
transmitting the current concentration of dissolved oxygen wirelessly to a hand-held device (9) of an operator, and
controlling the flow rate of the injected oxygen,
such that the measured current concentration approaches a pre-defined reference value, the device comprising:
the housing (100) configured to be submerged into the water (W),
wherein the housing (100) includes at least one water inlet (101),
an oxygen inlet (102), and
at least one water outlet (103) for discharging the oxygen enriched water stream (W") out of the housing (100);
the pump (5) being in fluid communication with the at least one water inlet (101) for sucking water (W) from the volume of water which is surrounding the housing (100),
wherein the pump (5) is configured to generate a main water stream (W');
means (200) for the injecting of the oxygen, the oxygen being supplied from the oxygen inlet (102) into the main water stream (W'); and
an oxygen probe (6) integrated into the housing (100) of the device (1);
wherein the oxygen probe (6) comprises a measuring surface (6a) for measuring the current concentration of the dissolved oxygen;
wherein the measuring surface (6a) is at a tip of the oxygen probe (6); and
wherein the device (1) is configured to direct a side water stream (S') of the main water stream (W') from a first orifice O at a junction between an outlet pipe of said pump and said means (200) for the injecting of the oxygen into the main water stream (W'), along the measuring surface (6a) for measuring the current concentration of the dissolved oxygen, and through a second orifice O' out of the housing.

* * * * *